United States Patent [19]

Bains et al.

[11] Patent Number: 5,026,934
[45] Date of Patent: Jun. 25, 1991

[54] METHOD FOR CONVERTING LIGHT HYDROCARBONS TO OLEFINS, GASOLINE AND METHANOL

[75] Inventors: Charanjit S. Bains, Houston; Martin P. Grosboll, Kingwood, both of Tex.

[73] Assignee: Lyondell Petrochemical Company, Houston, Tex.

[21] Appl. No.: 479,086

[22] Filed: Feb. 12, 1990

[51] Int. Cl.$^5$ ............ C07C 2/00; C07C 29/00; C07C 27/00
[52] U.S. Cl. .................... 585/314; 585/310; 585/324; 585/500; 585/640; 585/943; 568/840; 518/702; 252/373
[58] Field of Search .............. 585/500, 943, 640, 314, 585/310, 324; 518/702; 252/373; 568/840

[56] References Cited

U.S. PATENT DOCUMENTS

| | | | |
|---|---|---|---|
| 2,604,479 | 8/1949 | Rollman | 422/223 |
| 3,041,273 | 9/1953 | Smith et al. | 422/214 |
| 3,894,102 | 8/1973 | Chang et al. | 585/943 |
| 3,894,107 | 7/1973 | Butler et al. | 585/640 |
| 3,931,349 | 9/1974 | Kuo | 585/500 |
| 3,969,426 | 10/1974 | Owen et al. | 585/640 |
| 4,035,430 | 7/1976 | Dwyer et al. | 585/640 |
| 4,499,322 | 8/1983 | Jones et al. | 585/500 |
| 4,544,784 | 4/1984 | Sofranko et al. | 585/500 |
| 4,560,821 | 8/1984 | Jones et al. | 585/500 |
| 4,567,307 | 1/1985 | Jones et al. | 585/500 |
| 4,634,800 | 5/1985 | Withers, Jr. | 585/500 |
| 4,665,260 | 12/1985 | Jones et al. | 585/500 |
| 4,777,313 | 6/1986 | Sofranko et al. | 585/500 |
| 4,888,131 | 12/1989 | Goetsch et al. | 252/373 |
| 4,926,006 | 5/1990 | Kawamura et al. | 585/640 |

Primary Examiner—Anthony McFarlane
Assistant Examiner—Nhat Phan
Attorney, Agent, or Firm—Arnold, White & Durkee

[57] ABSTRACT

The invention provides a method of converting light hydrocarbons to olefins, gasoline and methanol. In the first stage, a gas containing one or more light hydrocarbons is synthesized to higher hydrocarbons including raw gasoline. However, at commercially acceptable selectivities using currently available catalyst, a majority of the light hydrocarbons remain unsynthesized. In addition, the synthesis produces significant quantities of carbon dioxide and some carbon monoxide. In this method the unsynthesized light hydrocarbons and the oxides of carbon are used to produce methanol, which can be used for several purposes including gasoline or ethylene synthesis.

46 Claims, 4 Drawing Sheets

METHOD FOR CONVERTING LIGHT HYDROCARBONS TO OLEFINS, GASOLINE AND METHANOL

BACKGROUND OF THE INVENTION

This invention relates to the synthesis of light hydrocarbons to higher hydrocarbons, including gasoline, at conversion levels that compliment secondary product utilization. The process uses unsynthesized light hydrocarbons, together with oxides of carbon produced as secondary products, to make methanol. The methanol and/or the higher hydrocarbons may then be used to make gasoline or ethylene.

Previous work on gasoline synthesis has concentrated on methane, because methane is a chemical in plentiful supply, natural gas being principally composed of methane. One known way of producing gasoline from methane, originally developed by Mobil Oil Company, is to first reform desulfurized natural gas to form hydrogen, carbon monoxide and carbon dioxide, otherwise known as synthesis gas or syngas. Methanol is then synthesized from the syngas by well established low pressure techniques. Gasoline is made by passing the methanol over a suitable catalyst, as disclosed in U.S. Pat. Nos. 3,894,107, 3,931,349 and related patents.

Another route, developed by the Atlantic Richfield Company (ARCO), involves first synthesizing higher olefins from methane, using a suitable oxidizing catalyst as disclosed in U.S. Pat. No. 4,777,313 and the patents listed therein. Some gasoline is produced by this synthesis, and the lower hydrocarbons produced by the synthesis can also be converted to gasoline. The main disadvantage of this method is that, at commercially acceptable selectivity, the methane conversion is relatively low. The solution adopted by ARCO was to recycle the unconverted methane, requiring a very large reactor/regenerator system. Further, the large amount of carbon dioxide produced in the synthesis was unused, being vented to the atmosphere. This means that much of the carbon from the methane is not converted to something useful. Further, the release of large amounts of carbon dioxide into the atmosphere could be environmentally detrimental.

SUMMARY OF THE INVENTION

This invention provides a method for converting light hydrocarbons, preferably hydrocarbons with up to four carbon atoms, to higher hydrocarbons and methanol, which comprises contacting a gas containing one or more of the light hydrocarbons at synthesizing conditions with an oxidative synthesizing agent to synthesize higher hydrocarbons from at least part of the light hydrocarbons, recovering the higher hydrocarbons, recovering carbon dioxide produced during the synthesis, mixing the recovered carbon dioxide with hydrogen and then contacting the mixture at methanol synthesizing conditions with an agent capable of synthesizing methanol, and recovering the methanol.

Preferably, the gas is not recycled, i.e. is contacted one time only, the light hydrocarbons that remain unsynthesized after this single contact being recovered. The recovered light hydrocarbons, together with carbon monoxide produced in the synthesis, is then reformed to hydrogen, carbon monoxide and carbon dioxide, which are mixed with the carbon dioxide recovered after the light hydrocarbon synthesis for the purpose of synthesizing to methanol. As an alternative to recovering the light hydrocarbons, all the remaining components of the synthesizing reactor effluent after the higher hydrocarbons and water have been removed are passed through the reformer.

In the preferred embodiment, the oxidative synthesizing agent comprises at least one reducible oxide of at least one metal selected from the group consisting of manganese, tin, indium, germanium, lead, antimony and bismuth, preferably manganese. It is advantageous if the oxidative synthesizing agent further comprises at least one promoter selected from the group consisting of alkali metals, alkaline earth metals and their compounds, preferably a compound of lithium. It is even more preferred that the oxidizing synthesizing agent further comprises at least one member of the group consisting of boron and compounds of boron.

The method of this invention may particularly be used to produce gasoline from light hydrocarbons. In one embodiment gas containing one or more light hydrocarbons is contacted at synthesizing conditions with an oxidative synthesizing agent to synthesize higher hydrocarbons including gasoline from at least part of the light hydrocarbons, and the gasoline and the higher hydrocarbons are separately recovered. Methanol is synthesized using the recovered carbon dioxide and reformed unsynthesized light hydrocarbons, the methanol is recovered and at least part of the methanol is converted to gasoline Alternatively, the method may be used to produce ethylene from light hydrocarbons, both as one product of the light hydrocarbons synthesis and also from conversion of at least part of the methanol to ethylene.

In another embodiment, the entire effluent from the synthesizinq reactor is contacted at suitable conditions with an agent capable of synthesizing gasoline from olefins. This agent is preferably a suitable fluidized zeolite catalyst. After removal of water, the gasoline and other hydrocarbons higher than methane and ethane are recovered. The remaining unreacted methane, ethane and carbon dioxide may be utilized, either to make methanol or as fuel for power generation or other uses.

An advantage of this method is that the carbon dioxide produced in the synthesis of higher hydrocarbons is utilized, rather than being wasted by being vented to the atmosphere with potentially adverse environmental effects. A further advantage of the preferred embodiment is that the light hydrocarbon feedstock which is not synthesized on the first pass through are not recycled to the synthesis reactor, thus permitting smaller and cheaper reactors requiring less catalyst to be used, but is still used to produce a useful product, methanol, at higher yields because of carbon dioxide utilization. The method has the further advantage of allowing flexibility in the products produced from the plant in which it is carried out, permitting a ready change in the mix of products as commercial economics change.

DETAILED DESCRIPTION OF THE INVENTION

The method of this invention can be used with any source of a light hydrocarbon, preferably a hydrocarbon with up to four carbon atoms, either pure or mixed other light hydrocarbons and/or with minor amounts of inert substances. In the preferred embodiment, the feedstock is natural gas which has been field treated by desulfurizing and by removing water and a proportion of the condensable hydrocarbons, generally propane and higher hydrocarbons. In an alternative embodiment, refinery offgas may be used.

Figure 1:
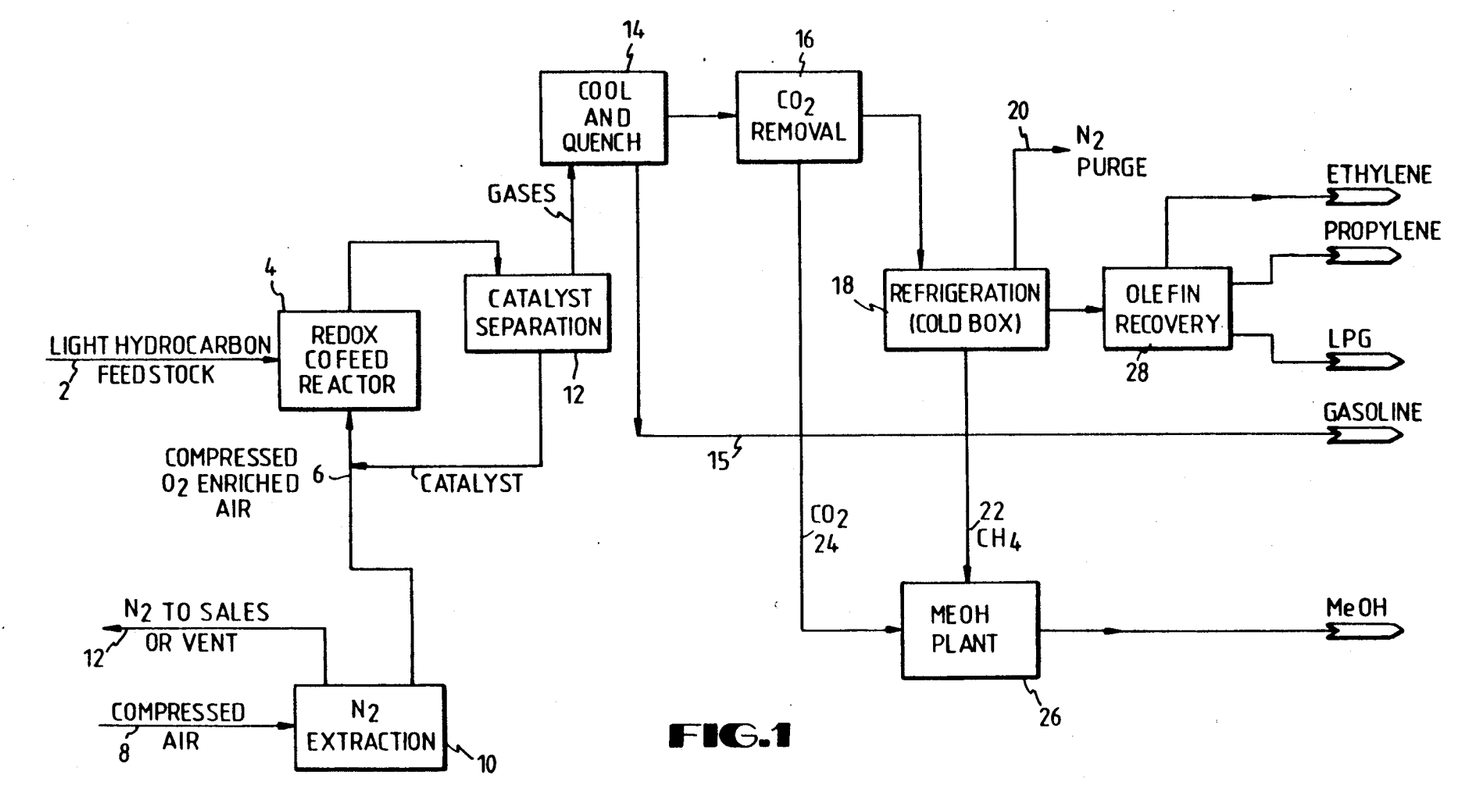
FIG. 1 is a diagrammatic representation of the process flow, using a co-feed reactor for the light hydrocarbon synthesis.

FIG. I shows diagrammatically the preferred embodiment of the method of the invention. The light hydrocarbon feedstock 2 is fed to the co-feed reactor 4, where it contacts a catalyst. The catalyst is comprised of a conventional support material carrying an oxidative synthesizing agent. The composition and preparation of preferred catalysts is described in U.S. Pat. Nos. 4,499,322 and 4,777,313, incorporated herein by reference, but other suitable known catalysts may be employed. Most preferably, the catalyst contains a manganese oxide as the oxidative agent, with a lithium compound and boron or a boron compound as promoters.

In a cofeed reactor the catalyst is reoxygenated in situ through the introduction of a source of oxygen into the reactor, co-fed with the light hydrocarbon feedstock. In the preferred embodiment, compressed, oxygen enriched air 6 is used, but air or pure oxygen are other possible oxygen sources. Oxygen enriched air may be provided from compressed air 8 by a suitable nitrogen extraction unit 10. Any known technology for providing oxygen enriched air may be used, including the pressure swing adsorption (PSA) method of nitrogen removal and/or a cryogenic air separation plant. Preferably, the nitrogen 12 is collected and sold or otherwise utilized.

Catalyst from the catalyst separation unit 12 is fed into the reactor 4, preferably in the stream of oxygen enriched air 6. The use of compressed air provides a fluidized upflow of catalyst. The light hydrocarbon feedstock 2, is introduced into the lower part of the reactor and the synthesis takes place while the catalyst and feedstock travel upward together. The preferred rate of conversion is between 25% and 35%.

From the reactor 4 the effluent passes through catalyst separation 12. The separated catalyst is recycled through the reactor 4. The gases are cooled and quenched 14, and raw gasoline 15 is condensed and separated at this stage. The gases then pass to a carbon dioxide removal unit 16. After removal of the carbon dioxide the gases pass to a refrigeration unit 18 to remove unreacted light hydrocarbons and secondary synthesis products. Nitrogen may also be separated at this stage and, if so, the nitrogen 20 is either vented or collected for use or sale. The light hydrocarbons 22, together with the carbon dioxide 24 removed in stage 16, are used to synthesize methanol in a conventional methanol plant 26.

The olefinic mixture from the refrigeration unit 18 is passed to a conventional olefin recovery unit 28, from which ethylene, propylene and other hydrocarbons such as LPG are recovered.

Figure 2:
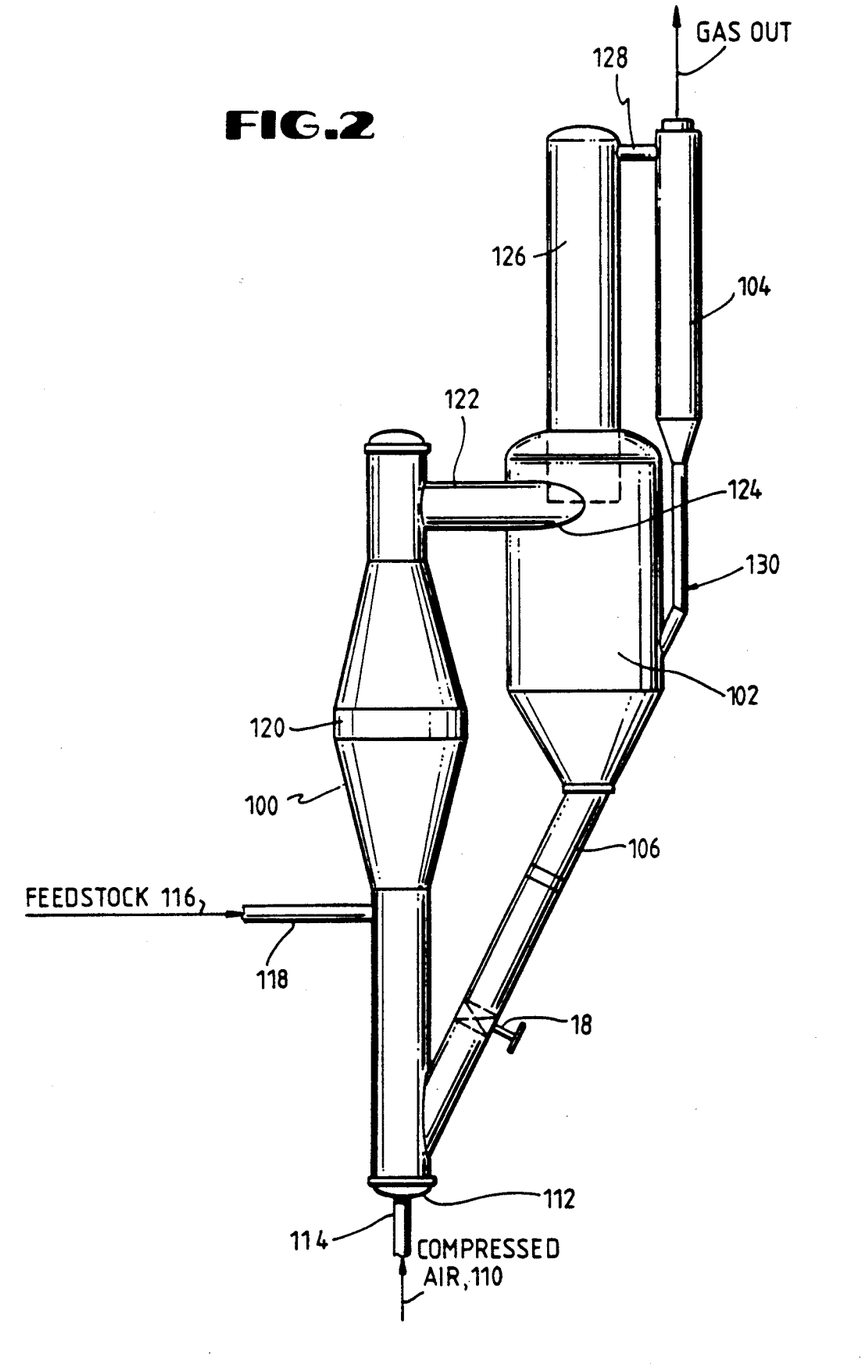
FIG. 2 is an elevation of a co-feed reactor design for use in the light hydrocarbon synthesis step of the process.

FIG. 2 shows a plan elevation of the preferred design for the co-feed reactor system. The preferred embodiment uses two trains, each containing a reactor vessel 100, a reactor stripper 102 and associated cyclones. The cyclones are designed to achieve better than 99.5% recovery of 20 micron solids. While a single cyclone 104 is shown in FIG. 2, it will be understood by those skilled in the solids separation art that additional cyclones may be needed to achieve desired levels of separation of solids from effluent gases.

Catalyst from the stripper 102 is gravity fed through catalyst feed pipe 106, controlled by slide valve 108. It is then lifted at high velocity, at preferably about 40 feet/second, by compressed air, oxygen or oxygen enriched air 110 which is injected into the riser base 112 of the reactor 100 through inlet 114.

The light hydrocarbon feed gas 116 is introduced into the reactor 100 at the point 118 at which the diameter of the reactor starts to increase. The increasing diameter of the reactor has the effect of reducing the velocity of the gas and catalyst mixture, in order to increase the catalyst residence time. The residence time needed to give the desired degree of conversion can be calculated for any set of actual conditions by those skilled in the art. In the preferred embodiment the velocity at the point of maximum diameter 120 is about 7 feet/second.

Preferably, the reactor operates at a temperature between about 1400°–1600° F., and at a pressure between about 30–80 PSIA. At start up, and for operation at low rates of conversion, the feed gas is preheated before introduction into the reactor. However, at high rates of conversion the reaction is exothermic, and the feed gas may be at ambient temperature.

After point 120 the reactor diameter decreases, thereby accelerating the effluent stream towards the reactor outlet pipe 122. This acceleration helps to decrease the catalysis of secondary reactions. In the preferred embodiment, the effluent stream is accelerated to about 40 feet/second. The effluent stream, which contains catalyst and gases including unsynthesized light hydrocarbons and synthesis products, is injected tangentially into stripper 102 through nozzle 124, which again accelerates the stream. In the preferred embodiment, the stream enters the stripper 102 at about 55 feet/second.

A bulk separation of the catalyst from the gases is achieved in the stripper 102. After stripping with steam to remove the residual hydrocarbons, the catalyst exits the stripper through catalyst feed pipe 106 to be recycled through reactor 100. The gaseous components, which still contain catalyst fines, rise through plenum 126, and exiting through plenum offtake pipe 128 are injected tangentially into cyclone 104. To minimize secondary reactions, the effluent stream is quenched with water in the reactor outlet pipe 122 and the plenum offtake pipe 128 to about 1400° F. Further separation of catalyst particles is effected in the cyclone, the separated catalyst particles being transferred to stripper 102 through pipe 130. The gas exiting from the top of the cyclone 104 is further separated from remaining catalyst fines by being passed through a series of two stage parallel cyclones to achieve the desired level of solids recovery, preferably in excess of 99.5% of solids of diameter 20 microns and larger.

Figure 3:
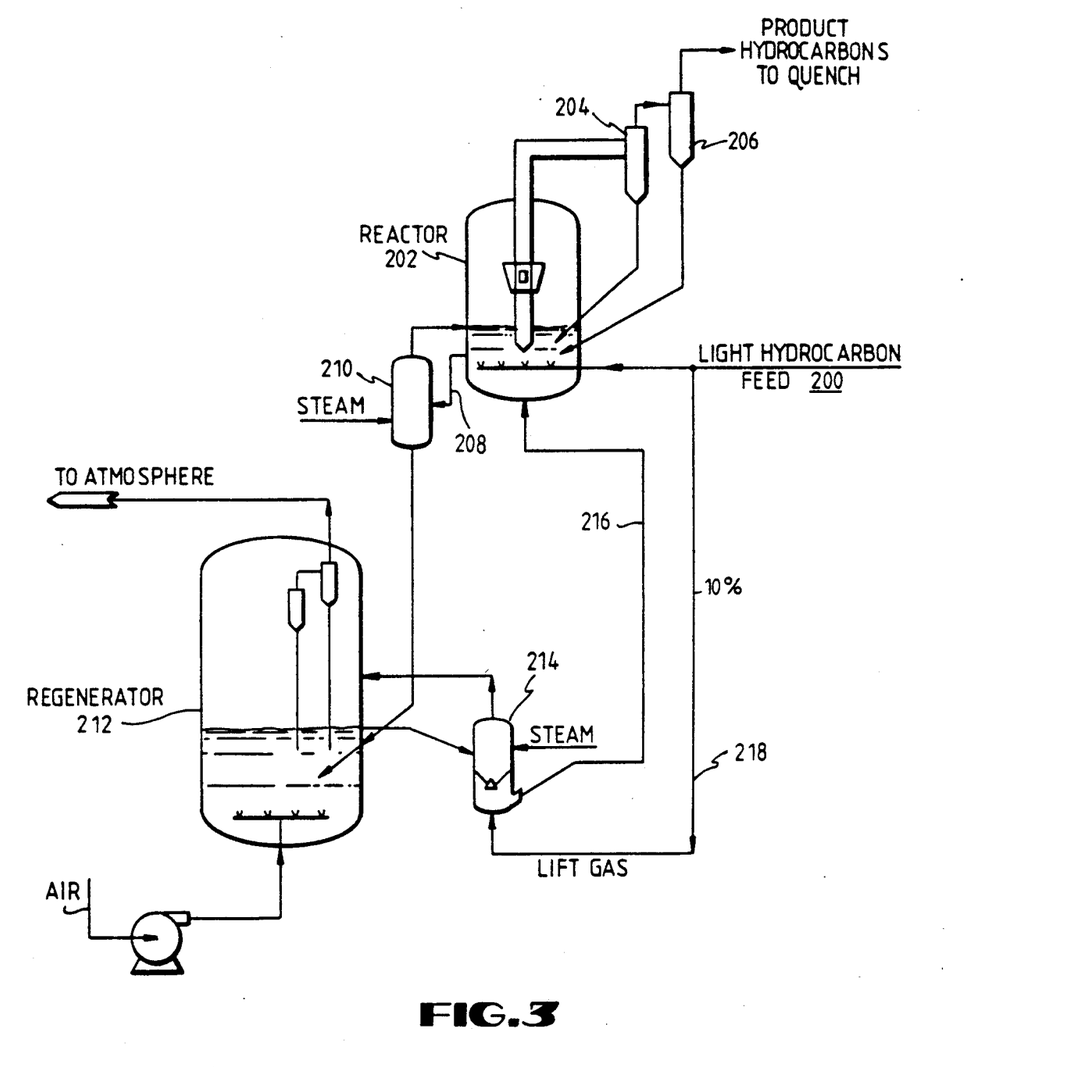
FIG. 3 is a schematic depiction of a two stage reaction system.

Instead of a cofeed reactor a two stage redox reactor may be used, in which the catalyst is reoxidized in a separate vessel from the reactor. One such reactor system is shown in FIG. 3. The light hydrocarbon feedstock 200 is fed into the lower part of reactor 202 which contains catalyst. The effluent gases leave the reactor and pass through a series of cyclones, represented here by cyclones 204 and 206, to separate out catalyst fines. Spent catalyst leaves the reactor through tube 208 and passes through stripper 210 which strips hydrocarbons from the catalyst before it enters the regenerator 212. The spent catalyst is there contacted by a source of oxygen, which could be air or a steam/air mixture, at an elevated temperature of about 1500° F. which causes the catalyst to become reoxidized. After passing through stripper 214 to remove nitrogen, the catalyst is lifted to the reactor 202 through lift feed pipe 216 by a portion of the feed stock 200 which is piped through lift feed gas supply 218.

The light hydrocarbon synthesis catalyst is known to be poisoned at high temperatures by iron, therefore it is preferred that all wetted surfaces in the reactor system be coated with suitable lining, such as a high alumina refractory.

After leaving the catalyst removal system, the gases are cooled to about 120° F. in a series of heat exchangers. If required, final removal of solids carried over from the reactor may be effected after this cooling by contacting the gas with a water spray and then passing it through a trayed tower. In the preferred embodiment the gas stream is then compressed to about 150 psi. Much of the water and heavy hydrocarbons in the stream are liquified at this stage and removed. Large quantities of water are produced which, after suitable treatment to remove hydrocarbons and other pollutants, may be used for industrial purposes.

The next step is carbon dioxide removal 16, which is preferably carried out using a conventional acid gas removal system based on aqueous methanolamine, DEA, MDEA and the like.

The hydrocarbon gas after carbon dioxide removal is then cooled to about 45° F. The water and hydrocarbons condensed at these conditions are separated, and the remaining water vapor and carbon dioxide removed, preferably using a molecular sieve dehydration system.

The hydrocarbon stream is then further refrigerated in a conventional cold box system 18. From this system ethylene and propylene are recovered as one product stream. This stream is further purified to remove trace compounds, compressed to about 400 psi, and then the ethylene is separated from the propylene using conventional ethylene separation techniques. In the preferred embodiment, cryogenic techniques suitable to produce polymer grade ethylene and propylene are utilized. Raw gasoline is condensed and produced as a separate stream before the cold box system.

The unreacted light hydrocarbons, together with secondary synthesis products, in particular carbon monoxide, are separately recovered from the cold box system. After recovery they may still be mixed with nitrogen, but in the preferred embodiment the cold box system is designed to separate the nitrogen, which is either purged or collected. The recovered gases are compressed to about 450 psi and is then passed to the reformer to convert the light hydrocarbons to synthesis gas. In the preferred embodiment a conventional tubular steam reformer is used. The synthesis gas from the reformer is then cooled to about 90° F., mixed with the carbon dioxide recovered in stage 16 which has been compressed to a similar pressure, and the mixture compressed to about 1200 psi and passed to the methanol synthesis system. Any suitable known methanol synthesis system may be used, the preferred embodiment uses a Linde AG design, isothermal reactor.

The gases leaving the methanol synthesis reactor are cooled to condense methanol and water, and a portion of the remaining gases are recycled to the synthesis reactor. The methanol is then separated from the water and purified by conventional techniques, preferably distillation. The degree of purification required will depend upon the eventual use for the methanol. The water may be treated as described above for further use.

Figure 4:
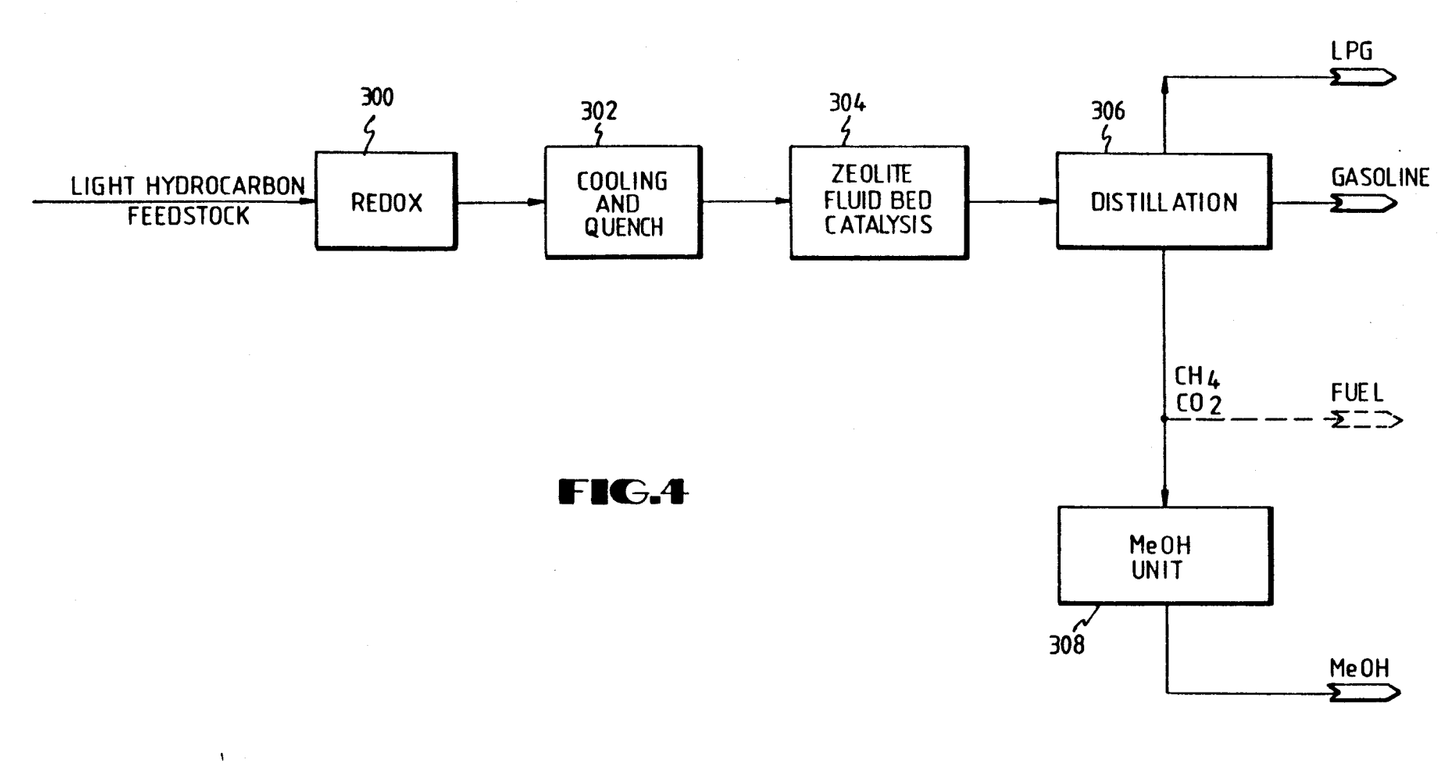
FIG. 4 is a diagrammatic representation of the process flow of an alternative method of utilizing the products of the light hydrocarbon synthesis.

In an alternative embodiment shown in FIG. 4, the products of the light hydrocarbon synthesis reactor 300 are cooled by conventional cooling and quenching means 302 to about 800° F. and then directed to a fluidized bed 304 containing a zeolite catalyst, preferably a ZSM-5 or equivalent catalyst. Here the olefins are converted to gasoline and LPG. The products of the reactor are cooled to separate water and all hydrocarbons higher than methane and ethane are recovered by conventional means 306. The unreacted gases, primarily methane and $CO_2$, are compressed and sent to a classical steam reforming methanol unit 308. Alternatively, the unreacted gases may be directed to a gas-turbine cogeneration unit for power and/or steam production, or be used as fuel for other purposes. This embodiment has cost advantages in that much less cooling equipment is required. Further the needed degree of separation of catalyst fines is not as great, requiring less separation equipment.

In either of the above-described embodiments, at least part of the methanol may be converted to gasoline, using a suitable zeolite catalyst. The preferred method is described in U.S. Pat. No. 3,894,107 owned by Mobil Oil Corporation and incorporated herein by reference, and the catalysts are described in U.S. Pats. Nos. 3,702,886 and 3,709,979. In the preferred embodiment a zeolite catalyst equivalent to the Mobil ZSM-5 catalyst is used, which is available commercially from a number of vendors. Alternatively, the methanol may be used to make ethylene. This is preferably done by a two stage process. In the first stage a suitable zeolite catalyst is used to convert the methanol to DMA, then in the second stage DMA is converted to ethylene using an activated alumina catalyst.

Additional advantages and modifications will be readily apparent to those skilled in the art. The invention in its broader aspects is therefore not limited to the specific details, representative apparatus or the illustrative example shown and described. Accordingly, departures may be made from the detail without departing from the spirit or scope of the disclosed general inventive concept.

What is claimed is:

1. A method for converting light hydrocarbons to higher hydrocarbons and methanol, which comprises:
   (a) contacting a gas containing one or more light hydrocarbons at synthesizing conditions with an oxidative synthesizing agent to synthesize higher hydrocarbons from at least part of the light hydrocarbons;
   (b) recovering the higher hydrocarbons;
   (c) recovering carbon dioxide produced during the synthesis, said higher hydrocarbons and carbon dioxide being recovered separately;
   (d) mixing the recovered carbon dioxide with hydrogen or synthesis gas;

(e) contacting the mixture comprising carbon dioxide at methanol synthesizing conditions with an agent capable of synthesizing methanol; and (f) recovering the methanol.

2. The method of claim 1, wherein the light hydrocarbons are selected from the group consisting of methane, ethane, propane, n-butane and isobutane.

3. The method of claim 1, wherein the gas is contacted one time only.

4. The method of claim 1, wherein the oxidative synthesizing agent comprises at least one reducible oxide of at least one metal selected from the group consisting of Mn, Sn, In, Ge, Pb, Sb, and Bi.

5. The method of claim 4, wherein the metal is Mn.

6. The method of claim 4, wherein the oxidative synthesizing agent further comprises at least one promoter selected from the group consisting of alkali metals, alkaline earth metals and compounds thereof.

7. The method of claim 6, wherein the promoter is a compound of Li.

8. The method of claim 6, wherein the oxidizing synthesizing agent further comprises at least one member of the group consisting of boron and compounds of boron.

9. A method for converting light hydrocarbons to higher hydrocarbons and methanol, which comprises:

(a) contacting a gas containing one or more light hydrocarbons at synthesizing conditions with an oxidative synthesizing agent to synthesize higher hydrocarbons from at least part of the light hydrocarbons;

(b) recovering the higher hydrocarbons;

(c) recovering carbon dioxide produced during the synthesis;

(d) recovering the light hydrocarbons that remain unsynthesized and carbon monoxide produced during synthesis;

(e) reforming at least part of the unsynthesized light hydrocarbons and carbon monoxide to provide hydrogen, carbon monoxide and carbon dioxide;

(f) mixing the recovered carbon dioxide with the products of the reformed unsynthesized light hydrocarbons;

(g) contacting the mixture at methanol synthesizing conditions with an agent capable of synthesizing methanol; and (h) recovering the methanol.

10. The method of claim 9, wherein the light hydrocarbons are selected from the group consisting of methane, ethane, propane, n-butane and isobutane.

11. The method of claim 9, wherein the gas is contacted one time only.

12. The method of claim 9, wherein the oxidative synthesizing agent comprises at least one reducible oxide of at least one metal selected from the group consisting of Mn, Sn, In, Ge, Pb, Sb, and Bi.

13. The method of claim 12, wherein the metal is Mn.

14. The method of claim 12, wherein the oxidative synthesizing agent further comprises at least one promoter selected from the group consisting of alkali metals, alkaline earth metals and compounds thereof.

15. The method of claim 14, wherein the promoter is a compound of Li.

16. The method of claim 14, wherein the oxidizing synthesizing agent further comprises at least one member of the group consisting of boron and compounds of boron.

17. The method of claim 9, further comprising the step of recovering water produced during the light hydrocarbon synthesis and methanol synthesizing steps.

18. A method for converting light hydrocarbons to higher hydrocarbons and methanol, which comprises:

(a) passing through a reactor vessel a gas containing one or more light hydrocarbons at synthesizing conditions so that the gas comes into contact with an oxidative synthesizing agent to synthesize higher hydrocarbons from at least part of the light hydrocarbons;

(b) removing water from the effluent exiting the reactor vessel;

(c) recovering from the reactor effluent the higher hydrocarbons and carbon dioxide produced during the synthesis;

(d) passing the remainder of the reactor effluent through a reformer to provide hydrogen, carbon monoxide and carbon dioxide;

(e) mixing the recovered carbon dioxide with the products from the reformer;

(f) contacting the mixture at methanol synthesizing conditions with an agent capable of synthesizing methanol; and (g) recovering the methanol.

19. The method of claim 18, wherein the light hydrocarbons are selected from the group consisting of methane, ethane, propane, n-butane and isobutane.

20. The method of claim 18, wherein the gas is passed one time only through the reactor vessel.

21. The method of claim 21, wherein the oxidative synthesizing agent comprises at least one reducible oxide of at least one metal selected from the group consisting of Mn, Sn, In, Ge, Pb, Sb, and Bi.

22. The method of claim 21, wherein the metal is Mn.

23. The method of claim 21, wherein the oxidative synthesizing agent further comprises at least one promoter selected from the group consisting of alkali metals, alkaline earth metals and compounds thereof.

24. The method of claim 23, wherein the promoter is a compound of Li.

25. The method of claim 23, wherein the oxidizing synthesizing agent further comprises at least one member of the group consisting of boron and compounds of boron.

26. A method of producing gasoline from light hydrocarbons, comprising:

(a) contacting a gas containing one or more light hydrocarbons at synthesizing conditions with an oxidative synthesizing agent to synthesize higher hydrocarbons including gasoline from at least part of the light hydrocarbons;

(b) recovering the gasoline (c) recovering the higher hydrocarbons;

(d) recovering carbon dioxide produced during the synthesis;

(f) reforming at least part of the unsynthesized light hydrocarbons to provide hydrogen, carbon monoxide and carbon dioxide;

(g) mixing the recovered carbon dioxide with the products of the reformed unsynthesized light hydrocarbons;

(h) contacting the mixture at methanol synthesizing conditions with an agent capable of synthesizing methanol;

(i) recovering the methanol; and (j) converting at least part of the methanol to gasoline.

27. The method of claim 26, wherein the light hydrocarbons are selected from the group consisting of methane, ethane, propane, n-butane and isobutane.

28. The method of claim 26, wherein the gas is contacted one time only.

29. The method of claim 26, wherein the oxidative synthesizing agent comprises at least one reducible oxide of at least one metal selected from the group consisting of Mn, Sn, In, Ge, Pb, Sb, and Bi.

30. The method of claim 29, wherein the metal is Mn.

31. The method of claim 29, wherein the oxidative synthesizing agent further comprises at least one promoter selected from the group consisting of alkali metals, alkaline earth metals and compounds thereof.

32. The method of claim 31, wherein the promoter is a compound of Li.

33. The method of claim 29, wherein the oxidizing synthesizing agent further comprises at least one member of the group consisting of boron and compounds of boron.

34. A method of producing ethylene from light hydrocarbons, comprising:
(a) contacting a gas containing one or more light hydrocarbons at synthesizing conditions with an oxidative synthesizing agent to synthesize higher hydrocarbons including ethylene from at least part of the light hydrocarbons;
(b) recovering the higher hydrocarbons;
(c) recovering carbon dioxide produced during the synthesis;
(e) reforming at least part of the light hydrocarbons that remain unsynthesized to provide hydrogen, carbon monoxide and carbon dioxide;
(f) mixing the recovered carbon dioxide with the products of the reformed unsynthesized light hydrocarbons;
(g) contacting the mixture at methanol synthesizing conditions with an agent capable of synthesizing methanol;
(h) recovering the methanol; and
(i) converting at least part of the methanol to ethylene.

35. The method of claim 34, wherein the light hydrocarbons are selected from the group consisting of methane, ethane, propane, n-butane and isobutane.

36. A method of producing gasoline from light hydrocarbons, comprising:
(a) passing a gas containing one or more light hydrocarbons through a reactor vessel at synthesizing conditions so that the gas comes into contact with an oxidative synthesizing agent to synthesize higher hydrocarbons including olefins from at least part of the light hydrocarbons;
(b) contacting the effluent exiting the reactor at synthesizing conditions with an agent capable of synthesizing gasoline from olefins;
(c) removing water from the product of the gasoline synthesis;
(d) recovering all hydrocarbons higher than methane and ethane.
(e) reforming the methane, ethane and carbon dioxide remaining after step (d) to provide hydrogen, carbon monoxide and carbon dioxide;
(f) contacting the reformer output at methanol synthesizing conditions with an agent capable of synthesizing menthanol; and
(g) recovering the methanol.

37. The method of claim 36, wherein the light hydrocarbons are selected from the group consisting of methane, ethane, propane, n-butane and isobutane.

38. The method of claim 36, further comprising the step of using the methane, ethane and carbon dioxide remaining after step (d) as fuel.

39. The method of claim 36, wherein the oxidative synthesizing agent comprises at least one reducible oxide of at least one metal selected from the group consisting of Mn, Sn, In, Ge, Pb, Sb, and Bi.

40. The method of claim 39, wherein the metal is Mn.

41. The method of claim 39, wherein the oxidative synthesizing agent further comprises at least one promoter selected from the group consisting of alkali metals, alkaline earth metals and compounds thereof.

42. The method of claim 41, wherein the promoter is a compound of Li.

43. The method of claim 39, wherein the oxidizing synthesizing agent further comprises at least one member of the group consisting of boron and compounds of boron.

44. The method of claim 36, wherein the agent capable of synthesizing gasoline from olefins is a suitable zeolite catalyst.

45. In an improved method for converting light hydrocarbons to higher hydrocarbons and methanol wherein a gas containing one or more light hydrocarbons is passed at synthesizing conditions over an oxidative synthesizing agent to synthesize higher hydrocarbons, the improvement which comprises:
(a) passing the gas one time only over the synthesizing agent;
(b) recovering the higher hydrocarbons;
(c) recovering carbon dioxide produced during synthesis;
(d) recovering the light hydrocarbons that remain unsynthesized and carbon monoxide produced during synthesis;
(e) reforming at least part of the unsynthesized light hydrocarbons and carbon monoxide to hydrogen, carbon monoxide and carbon dioxide
(f) mixing the recovered carbon dioxide with the products of the reformed unsynthesized light hydrocarbons;
(g) contacting the mixture at methanol synthesizing conditions with an agent capable of synthesizing methanol;
(h) recovering the methanol.

46. In an improved method for converting light hydrocarbons to gasoline wherein a gas containing one or more light hydrocarbons is passed at synthesizing conditions over an oxidative synthesizing agent to synthesize higher hydrocarbons including gasoline, the improvement which comprises:
(a) passing the gas one time only over the synthesizing agent;
(b) recovering the higher hydrocarbons;
(c) separating the gasoline from the recovered higher hydrocarbons;
(d) recovering carbon dioxide produced during synthesis;
(e) recovering the light hydrocarbons that remain unsynthesized and carbon monoxide produced during synthesis;
(f) reforming at least part of the unsynthesized light hydrocarbons and carbon monoxide to hydrogen, carbon monoxide and carbon dioxide;

(g) mixing the recovered carbon dioxide with the products of the reformed unsynthesized light hydrocarbons;

(h) contacting the mixture at methanol synthesizing conditions with an agent capable of synthesizing methanol;

(i) recovering the methanol; and (j) converting at least part of the methanol to gasoline.

* * * * *